US00RE42395E

(19) United States
(12) Reissued Patent
Wright et al.

(10) Patent Number: US RE42,395 E
(45) Date of Reissued Patent: May 24, 2011

(54) VALVE HOLDER FOR TRICUSPID HEART VALVE

(75) Inventors: John Thomas Matthew Wright, Denver, CO (US); George Moreno Acosta, Menifee, CA (US); Jeffrey James Giba, Moreno Valley, CA (US)

(73) Assignee: Medtronic, Inc., Minneapolis, MN (US)

(21) Appl. No.: 11/907,535

(22) Filed: Oct. 12, 2007

Related U.S. Patent Documents

Reissue of:
(64) Patent No.: 7,018,407
Issued: Mar. 28, 2006
Appl. No.: 06/316,203
Filed: Oct. 29, 1981

(51) Int. Cl.
*A61F 2/24* (2006.01)
(52) U.S. Cl. ..... 623/2.11
(58) Field of Classification Search ..... 623/2.1, 623/FOR. 101
See application file for complete search history.

(56) References Cited

U.S. PATENT DOCUMENTS

| | | | | | |
|---|---|---|---|---|---|
| 3,099,016 | A | * | 7/1963 | Edwards | 623/2.4 |
| 3,263,239 | A | * | 8/1966 | Edwards et al. | 623/2.35 |
| 3,365,728 | A | * | 1/1968 | Edwards et al. | 623/2.4 |
| 3,409,013 | A | | 11/1968 | Berry | |
| 3,466,671 | A | * | 9/1969 | Siposs | 623/2.35 |
| 3,509,582 | A | * | 5/1970 | Pierie et al. | 623/2.35 |
| 3,534,410 | A | * | 10/1970 | Raible | 623/2.35 |
| 3,570,014 | A | * | 3/1971 | Hancock | 623/2.18 |
| 3,628,535 | A | | 12/1971 | Ostrowsky | |
| 3,656,185 | A | * | 4/1972 | Carpentier | 623/2.36 |
| 3,710,744 | A | * | 1/1973 | Goodenough et al. | 112/470.14 |
| 3,723,996 | A | * | 4/1973 | Raible et al. | 623/2.35 |
| 3,755,823 | A | * | 9/1973 | Hancock | 623/2.18 |
| 3,755,829 | A | * | 9/1973 | Hancock | |
| 4,106,129 | A | * | 8/1978 | Carpentier et al. | 623/2.18 |
| 4,185,636 | A | * | 1/1980 | Gabbay et al. | 606/148 |
| 4,865,600 | A | * | 9/1989 | Carpentier et al. | 623/2.11 |

FOREIGN PATENT DOCUMENTS

GB 2 011 259 A * 7/1979

OTHER PUBLICATIONS

The Annals of Thoracic Surgery, A Method for Insertion of a Stented Xenograft Valve in the Atrioventricular Position, George Stefanik, M.D., et al., pp. 166-167 (Jan.-Jun. 1976).*
The Annals of Thoracic Surgery, Stented Xenograft Valve Insertion, Edward Proctor, M.D., et al., vol. 29, No. 4, Apr. 1980, 2 pages.*
The Annals of Thoracic Surgery, Entanglement of Sutures with Struts of Mitral Bioprosthesis: How to Prevent It, N. Spampinato, M.D., et al., 1980, by the Society of Thoracic Surgeons, pp. 478-479 (Jan-Jun. 1981).*

(Continued)

*Primary Examiner* — David H. Willse
(74) *Attorney, Agent, or Firm* — McDermott Will & Emery LLP

(57) ABSTRACT

A holding device for a tricuspid prosthetic tissue heart valve which permits the commissure support struts to be drawn toward one another by increasing the tension on the threads which attach the holder to the valve. The resulting tapered valve configuration facilitates valve insertion and reduces the possibility of damaging the valve tissue during implantation.

21 Claims, 1 Drawing Sheet

OTHER PUBLICATIONS

The Annals of Thoracic Surgery, Prevention of "Strut-Snagging" during Mitral Valve Replacement with Stented Tissue Valves, Joseph B. Borman, M.B. B.Ch. (Wits.), F.R.C.S., et al., vol. 32, No. 2, pp. 209-210 (Aug. 1981).*

The Annals of Thoracic Surgery, Safer Insertion of Ionescu-Shiley Valves in the Atrioventricular Position, Graham N. Morritt, F.R.C.S. et al., pp. 94-95 (Jan.-Jun. 1982).*

The Annals of Thoracic Surgery, Posterior Midventricular Rupture after Mitral Valve Replacement, Gordon Katske, M.D., et al., vol. 27, No. 2, pp. 230-232 (Feb. 1979).*

The Annals of Thoracic Surgery, Delayed Rupture of the Left Ventricle after Mitral Valve Replacement with Bioprosthesis, L. Nunez, M.D., et al., vol. 27, No. 5, pp. 465-466 (May 1979).*

Carpentier-Edwards Bioprosthesis, Glutaraldehyde-Preserved Flexible Support-Mounted Porcine Valves, American Edwards Laboratories, pp. 1118-1129 (Aug. 1980, Prev. Rev. Jan. 1979).*

Package Insert #106259-2 Rev. B, American Edwards Laboratories, "Instructions For Use of the Handle/Holder Assembly For the Carpentier-Edwards Mitral Bioprosthesis", four pages.*

Starr-Edwards and Carpentier-Edwards, Ancillary Equipment for Cardiac Prostheses, Edwards Laboratories, pp. 1-4 (Oct. 1976, Prev. Rev. Sep. 1976).*

Instructions for Use of the Handle/Holder Assembly, For the Carpentier-Edwards Aortic Bioprosthesis, Edwards Laboratories, pp. 1-2 (Feb. 1980, Prev. Rev. Dec. 1979).*

A Suture Holder and Separator Attachment To The Starr-Edwards Prosthetic Valve Holders, J.T. Grismer, M.D., and G.W. Lillehei, M.D., F.A.C.S., Surgery, Gynecology and Obstetrics, pp. 583-584 (Mar. 1965).*

Package Insert #106259-2 Rev. B, American Edwards Laboratories, Instructions For Use of the Handle/Holder Assembly For the Carpentier-Edwards® Mitral Bioprosthesis.

A Suture Holder and Separator Attachment To The Srarr-Edwards Prosthetic Valve Holders, J.T. Grisner, M.D., and G.W. LilleiHei, M.D. Surgery, Gynecology and Obstetrics, pp. 583-584 (Mar. 1965).

Annals of Thoracic Surgery, A Method for Insertin of a Stented Xenograft Valce in the Atrioventicular Position, George Stefanik, M.D., et al., pp. 166-167 (Jan.-Jun. 1976).

Annals of Thoracic Surgery, Entanglement of Sutures with Struts of Mitral Bioprothesis: How to Prevent, N. Spampinato, M.D. et al., 1980 by the Society of Thoracic Surgeons, pp. 478-479, (Jan.-Jun. 1981).

Annals of Thoracic Surgery, Prevention of "Strut-Snagging" during Mitral Valve Replacement with Stented Tissue Valves, Joseph B. Borman, M.B.B.Ch. (Wits.) et al., vol. 32, No. 2, pp. 209-210, (Aug. 1981).

Annals of Thoracic Surgery, Safer Insertion of Ionescu-Shiley Valves in the Atrioventricular Position, Graham N. Morritt, F.R.C.S. et al., pp. 94-95 (Jan.-Jun. 1982).

Annals of Thoracic Surgery, Posterior Midventricular Rupture after Mitral Valve Replacemenr, Gordon Katske, M.D., et al., vol. 27, No. 2, pp. 230-232 (Feb. 1979).

Annals of Thoracic Surgery, Delayed Rupture of the Left Ventricle after Mitral Valve Replacement with Bioprosthesis, L. Nunez, M.D., et al., vol. 27, No. 5 (May 1979) pp. 465-466.

Carpentier-Edwards® Bioprostheses, Glutaraldehyde-Preserved Flexible Support-Mounted Porcine Valves, American Edwards Laboratories, pp. 1118-1129, (Aug. 1980, Prev. Rev. Jan. 1979).

* cited by examiner

VALVE HOLDER FOR TRICUSPID HEART VALVE

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to prosthetic heart valves and more particularly to a device for holding and positioning the heart valve during surgical implantation.

2. Description of Prior Art

Natural heart valves taken from animals, particularly porcine heart valves, have been widely used for several years in the replacement of diseased valves in humans. The porcine valve suitably treated with gluteraldehyde or other fixative solution is mounted on a cloth covered stent or supporting framework prior to implantation. The stent is typically an open cylindrical device having a gently scalloped base curve and three axially extending commissure support struts adapted to support the margins of the valve cusps as illustrated in U.S. Pat. No. 3,570,014. The stent is constructed of metal or plastic, covered with a cloth material, and provided with a circumferential sewing cushion extending outward from the base.

To facilitate handling of the valve during implantation, valve manufacturers have provided various valve holding devices which attach to the valve and allow the surgeon to more easily place the mounting sutures and position the valve in the original valve annulus. Once the valve and sutures are in position, the valve holder is detached from the valve and the surgical implantation procedure is completed.

Valve holders of the prior art consist in general of a support member sutured to the sewing cushion of the valve and an elongated handle which attaches to the support member by screw threads or other suitable means. The valve holder is separated from the valve by cutting the attaching sutures and withdrawing the handle and support member from the operating area. The handle may optionally include an elbow or other means to permit the valve to be angled relative to the main axis of the handle.

In mitral and tricuspid valve replacement, the prosthetic valve is inserted into position with the cusps directed away from the surgeon. In this position the cusps of the valve are subject to damage from snagging in the surrounding anatomical profile as the valve is moved into position and difficulty is sometimes encountered in inserting the valve into the original valve annulus. The mounting sutures are also suseptible to looping over the commissure posts as the valve is moved into position. Even with the aid of a valve holder, placing the valve in position is a sensitive and delicate procedure.

It is accordingly an object of the present invention to provide a valve holder for natural tissue prosthetic heart valves. It is a further object of this invention to provide a holder for mitral and tricuspid valves which facilitates the positioning of the valve within the original valve annulus. It is a yet further object of the present invention to provide a valve holder which permits the commissure support struts of the valve stent to be drawn toward one another prior to placement of the valve, thereby reducing the diameter of the leading portion of the valve and the possibility of snagging the valve cusps and damaging the delicate valve tissue. These and other objects of the invention will be apparent from the ensuing description and claims.

SUMMARY

The valve holder of the present invention consists of a central support member having three spaced valve support legs extending radially therefrom. A foot at the distal end of each leg is provided with thread guiding and attaching means. The central support member is provided with thread collecting means.

The valve holder is positioned on the sewing cushion of the valve stent with the legs of the holder in registry with the commissure support struts. The foot of each support leg is secured to the sewing cushion by means of retention threads which are placed through the valve holder and valve stent as follows.

The free end of one thread which is preferably a size 4-0 braided polyester suture is secured to the thread collection means of the central support member and passed through the guide means in the foot of one valve support leg and on through the underlying sewing cushion of the stent. The thread proceeds through the fabric cover at the tip of the proximate commissure support strut, across the valve orifice area to the tip of an adjacent commissure support strut, through the fabric cover at the tip of said strut and thence through the sewing cushion and overlying foot of the corresponding adjacent valve support leg. The end of the suture is thereupon attached to the foot of that support leg. The procedure is repeated with two additional sutures which are attached respectively to the remaining two suture legs.

When all of the sutures have been placed as described above, the valve holder may be drawn tightly against the sewing cushion of the stent by activating the thread collecting means to take up any slack in the sutures. Further activation of the thread collecting means will result in increased tension on the sutures with the tips of the commissure support struts being drawn inward to impart a tapered configuration to the valve. This taper permits the valve to be guided-into the original valve annulus more easily and with minimum danger of snagging or damaging the delicate valve cusp tissue. The retention threads extending across the valve orifice area between commissure support struts also reduce the possibility of the mounting sutures looping over the struts.

Once the valve is positioned in the annulus of the patient and the surgeon is ready to remove the valve holder, each retention thread is cut at the point between the foot of the valve support leg and the central support area. As the threads are cut, the commissure support struts are released from the restraints imposed by the threads and return to their normal configuration. The valve holder and handle are then separated from the valve with the loose ends of each thread remaining attached to the valve holder and being withdrawn from the valve as the holder is removed.

DESCRIPTION OF PREFERRED EMBODIMENTS

Figures 1, 2, 3, 4, 5, 6, 7, 8:
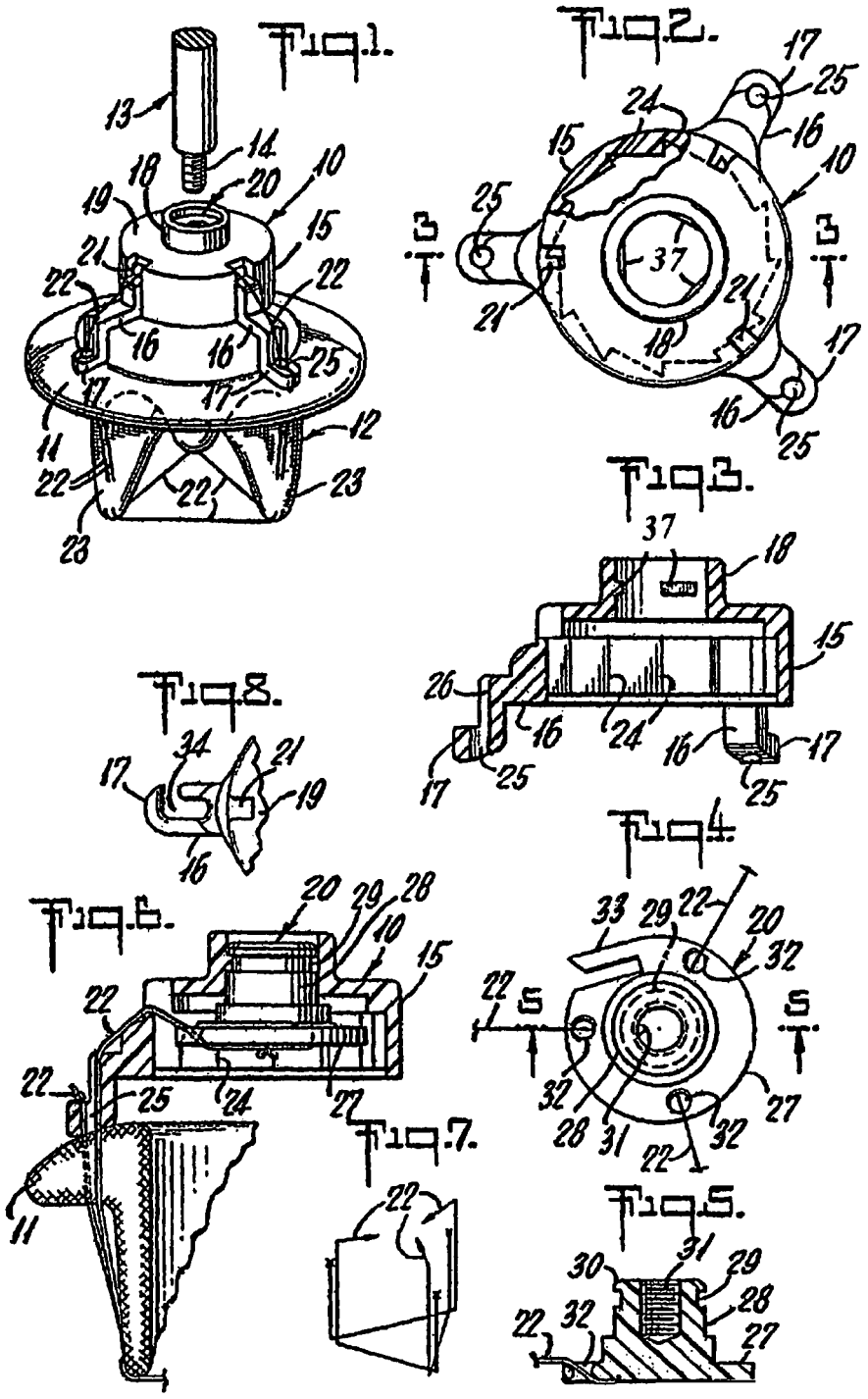
FIG. 1 is a view in perspective of the valve holder of the present invention attached to a mitral heart valve stent.
FIG. 2 is a plan top view in partial section of the valve holder of FIG. 1.
FIG. 3 is a side elevation view in cross section through the valve holder of FIG. 2 taken on line 3—3.
FIG. 4 is a top plan view of the thread collecting means utilized in the valve holder of FIG. 1.
FIG. 5 is a side elevation view in cross section of the thread collecting means of FIG. 4 taken through line 5—5.
FIG. 6 is a partial side elevation view in cross section of the valve holder and stent of FIG. 1 taken through one leg thereof.
FIG. 7 is a schematic view in perspective of the suture configuration securing the valve holder to the valve stent as illustrated in FIG. 1.
FIG. 8 is an enlarged top plan view of an alternate foot configuration for a valve support leg.

Referring now to FIG. 1, there is illustrated valve holder 10 attached to the sewing cushion 11 of valve stent 12. For clarity of illustration, the porcine tissue valve ordinarily mounted within the confines of the stent has been omitted from the drawings. Handle 13' shown in part is attachable to the valve holder by means of screw threads 14.

Valve holder 10 consists of a central support member 15 and three valve support legs 16 (two visible in FIG. 1) extending radially outward from the central support member. Each leg terminates in a foot 17 which includes thread guide and attachment means 25 in the form of a circular opening. Central support member 15 consists of a cylindrical structure having one open end facing stent 12 and terminating at the other end in coaxial hub 18 extending outward from annular flange 19. Positioned within the confines of the central support member is thread collecting disc 20 which includes stub axle 28 extending into hub 18 as illustrated in detail in FIGS. 4-6.

With further reference to FIG. 1, threads 22 are secured at one end to the thread collecting disc housed within the confines of the central support member and pass outward through windows 21 in the wall of member 15. Each thread passes through a guide means 25 in foot 17 of each respective valve support leg and thence through the underlying sewing cushion of the valve stent. Each thread continues to the tip or apex of the proximate commissure support strut where it passes briefly through cloth cover 23 and thereafter across the valley between commissure support struts to the next adjacent strut. The thread passes through the cloth cover at the tip of the adjacent commissure support strut and thence through the sewing cushion and foot portion of the overlying valve support leg, whereupon it is secured to the foot of said leg at thread attaching means 25.

Thread guide and attaching means 25 in the foot of each valve support leg is more clearly illustrated in FIG. 2 which is a top plan view of the valve holder of FIG. 1, and FIG. 3 which is a cross section of FIG. 2. In the illustrated embodiment, openings 25 extend into outwardly facing channels (or angled slot) 26 in the leg portion immediately adjacent the foot, and such channels 26 are effective to guide the threads over the knee of the leg.

The inner wall of central support cylinder 15 preferably includes a ratchet surface as illustrated in FIG. 2 which, in cooperation with a pawl on the thread collection means, permits rotation of the collection means in only one direction. This construction is most clearly illustrated in FIGS. 2 and 3 where the ratchet surface is indicated at 24.

Referring now to FIGS. 4 and 5, thread collecting means 20 is illustrated in detail and consists of a base plate 27 having stub axle 28 extending from one side thereof. Base plate 27 is further provided with pawl 33 which in the assembled valve holder engages ratchet teeth 24 to restrict rotation of the thread collection device. Base plate 27 is further provided with drill holes 32 as means for attaching one end of threads 22.

Also illustrated in FIGS. 2 and 3 are circumferential cleats 37 extending from the inner wall of hub 18, which in cooperation with a circumferential groove in the stub axle of the thread collecting disc, provide a snap fit to restrain the disc against axial displacement while permitting free rotation. The circumferential groove of the axle 28 is indicated at 29 in FIG. 5 which is a cross section through the center of the thread collecting device. Axle 28 is further provided with threaded drill hole 31 adapted to receive the screw threads of handle 13 as illustrated in FIG. 1.

The assembled valve holder is illustrated in cross section in FIG. 6 which further illustrates the path of threads 22 proceeding from the central support area through the thread guide means in the foot of each leg of the valve holder and thence through the sewing cushion and cloth covering at the tip of the commissure support struts. The two threads illustrated in FIG. 6 are, as explained above, two of three individual threads used to attach the valve holder to the valve stent. The configuration of the three threads in the assembled device is illustrated schematically in FIG. 7 where X indicates the end of the thread tied to the foot of the valve support leg and indicates the end of the thread attached to the thread collection device.

The thread guide and attaching means in the foot of each valve support leg may be a simple drill hole as illustrated in FIG. 2 or a channelled opening as illustrated at 34 in FIG. 8.

The retention thread configuration as described and illustrated above results in the tips of the stent commissure support struts being drawn together as the thread collection device is rotated to wind one end of each thread around stub axle 28. By thus reducing the spread of the commissure support struts, placement of the valve in a confined area is facilitated and the possibility of damaging the delicate tissue of the valve mounted within the confutes of the stent is reduced. To release the valve after it is positioned within the valve annulus, each thread is cut at a convenient spot over the valve support leg. As the thread tension is released the commissure support struts return to their normal spread. The threads passing through the valve stent remain securely attached to the valve support legs and the cut ends are withdrawn from the stent as the holder is removed from the area.

The preceding description and drawings are to a specific preferred embodiment of the present invention and are not for purposes of limitation. The key element of the present invention resides in the combination of the valve holder and the attaching threads which permit the threads to be collected by the valve holder in order to draw the tips of the commissure support struts toward each other and provide a tapered valve configuration.

What is claimed is:

1. A valve holder comprising a central support member, three spaced valve support legs extending radially from said support member, each of said legs including thread guiding and attaching means at a distal end thereof, and thread collecting means associated with said central support member and adapted to collect threads passing through the thread guiding means of said valve support legs, said central support member comprises a hub and annular flange extending therefrom, said hub being adapted for association with said thread collecting means, said thread collecting means comprising an axle rotatable in said hub of said central support member whereby threads passing through the thread guiding means of said valve support legs are collected by rotating said axle to wind said threads therein.

2. The valve holder of claim 1 wherein said thread collecting means includes a base plate coaxially affixed at the one end of said axle, said base plate having thread attaching means incorporated therein.

3. The valve holder of claim 2 wherein said central support member includes a cylindrical skirt depending from said annular flange and encircling the base plate of said thread collecting means, said skirt including three apertures in registry with said valve support legs for the passage of thread.

4. The valve holder of claim 3 wherein the inner wall of said cylindrical skirt includes ratchet teeth and the base plate of said thread collecting means includes a pawl adapted to engage said teeth and permit rotation of said thread collecting means in one direction only.

5. The valve holder of claim 1 wherein the hub of said central support member and the axle of said thread collecting means include cooperating elements to resist axial displacement while permitting free rotation of said thread collecting means.

6. The valve holder of claim 5 wherein said cooperating elements comprise a circumferential groove in said axle and inward projecting cleats in said hub adapted to engage said groove.

7. The valve holder of claim 1 wherein said axle is drilled and tapped to receive a threaded spindle of a handle member.

[8. A valve holder comprising a central support member, three spaced valve support legs extending radially from said support member, each of said legs including thread guiding and attaching means at a distal end thereof, and thread collecting means associated with said central support member and adapted to collect threads passing through the thread guiding means of said valve support legs, said thread guiding and attaching means comprise an angled slot in the distal end of each valve support leg.]

9. A valve holder comprising a centrally positioned cylindrical support element having one open end, a coaxial hub extending from the other end of said cylindrical support element and joined together by a radial flange;

coaxial thread [collecting means] *holding surface* encircled by said cylindrical support element and rotatably secured thereto;

at least three circumferentially spaced valve support legs extending radially from said cylindrical *support* element, each of said legs including thread guiding and attaching means at a distal end thereof; and thread passage means in said cylindrical element in registry with each of said valve support legs.

10. The valve holder of claim 9, wherein said thread [collecting means] *holding surface* comprises a base plate and stub axle extending from one side thereof, said axle extending into and being rotatably secured within the hub of said cylindrical element.

11. The valve holder of claim 10 wherein the inner wall of said cylindrical element includes ratchet teeth and the base plate of said thread [collecting means] *holding surface* includes a pawl adapted to engage said teeth and permit rotation of said thread [collecting means] *holding surface* in only one direction.

12. The valve holder of claim 10 wherein the axle of the thread [collecting means] *holding surface* and hub of said cylindrical support element include cooperating interacting means to resist axial displacement while permitting free rotation.

13. The valve holder of claim 12 wherein said cooperating elements comprise a circumferential groove in said axle and inward projecting cleats in said hub adapted to engage said groove.

14. The valve holder of claim 9 wherein said cylindrical element includes thread passages through the wall thereof in registry with said valve support legs.

15. In combination, a porcine tissue heart valve and a valve holder; said valve including a stent comprising a sewing cushion and three fabric covered, axially extending commissure support struts;

said valve holder comprising a central support member, three spaced valve support legs extending radially from said support member, each of said legs including thread guiding and attaching means at a distal end thereof, and thread collecting means associated with said central support member and adapted to collect threads passing through the thread guiding means of said valve support legs;

said central support member comprising a hub and annular flange extending therefrom, said hub being adapted for association with said thread collecting means, said thread collecting means of said valve holder comprising an axle rotatable in said hub of said central support member, said valve holder being positioned on the sewing cushion of said valve with valve support legs in registry with said commissure support struts and attached to said sewing cushion by means of threads, each of said threads being attached at one end to the distal end of a valve support leg and passing therefrom through said sewing cushion, thence through the fabric cover at a tip of the corresponding commissure support strut, thence extending to the next adjacent commissure support strut and passing through the fabric cover at the tip thereof, thence passing through sewing cushion and through the thread guiding means in the distal end of the corresponding valve support leg, and thereupon extending to and being attached to said thread collecting means, whereupon the tips of the commissure support struts are drawn toward one another as said threads passing through the thread guiding means of said valve support legs are collected by rotating said axle to wind said threads together.

16. The combination of claim 15 wherein said thread collecting means includes a base plate coaxially affixed at one end of said axle, said base plate having thread attaching means incorporated therein.

17. The combination of claim 16 wherein said central support member includes a cylindrical skirt depending from said annular flange and encircling the base plate of said thread collecting means, said skirt including three apertures in registry with said valve support legs for the legs for the passage of thread.

18. The combination of claim 17 wherein the inner wall of said cylindrical skirt includes ratchet teeth and the base plate of said thread collecting means includes a pawl adapted to engage said teeth and permit rotation of thread collecting means in one direction only.

19. A valve holder comprising a central support member, three spaced valve support legs extending radially from said support member, each of said legs including thread guiding and attaching means at a distal end thereof, and *a* thread [collecting means] *holding surface* rotatably mounted [with respect to] *and centrally disposed within* said central support member and adapted to [collect] *hold* threads passing through the thread guiding means of said valve support legs.

20. The valve holder of claim 19 wherein said thread guiding and attaching means comprise an aperture in the distal end of each valve support leg.

21. The valve holder of claim 19 wherein said thread guiding and attaching means comprise an angled slot in the distal end of each valve support leg.

22. In combination, a tricuspid prosthetic heart valve and a valve holder;

said valve including a stent comprising a sewing cushion and three fabric covered, axially extending commissure support struts;

said valve holder comprising a central support member, three spaced valve support legs extending radially from said support member, each of said legs including thread guiding and attaching means at a distal end thereof, and thread collecting means rotatably mounted with respect to said central support member and adapted to collect threads passing through the thread guiding means of said valve support legs;

said valve holder being positioned on the sewing cushion of said valve with the valve support legs in registry with said commissure support struts and attached to said sewing cushion by means of threads, each of said threads being attached at one end to the distal end of a valve support leg and passing therefrom through said sewing cushion, thence through the fabric cover at a tip of the corresponding commissure support strut, thence extending to the next adjacent commissure support strut and passing through the fabric cover at the tip thereof, thence passing through sewing cushion and through the thread guiding means in the distal end of the corresponding valve support leg, and thereupon extending to and being attached to said thread collecting means, whereupon the tips of the commissure support struts are drawn toward one another as said threads are collected by said thread collecting means.

* * * * *